United States Patent [19]
Muellen et al.

[11] Patent Number: 5,677,417
[45] Date of Patent: Oct. 14, 1997

[54] TETRAAROXYPERYLENE-3,4,9,10-TETRACARBOXYLIC POLYIMIDES

[75] Inventors: Klaus Muellen, Cologne, Germany; Dobrinka Todorova Dotcheva, Sofia, Bulgaria; Markus Klapper, Ruesselsheim, Germany

[73] Assignee: Max-Planck-Gesellschaft zur Foerderung, Munich, Germany

[21] Appl. No.: 513,769

[22] PCT Filed: Apr. 28, 1994

[86] PCT No.: PCT/EP94/01345

§ 371 Date: Aug. 29, 1995

§ 102(e) Date: Aug. 29, 1995

[87] PCT Pub. No.: WO94/25504

PCT Pub. Date: Nov. 10, 1994

[30] Foreign Application Priority Data

May 4, 1993 [DE] Germany .................. 43 14 622.8

[51] Int. Cl.⁶ .................. C08G 69/08; C08G 73/10
[52] U.S. Cl. .................. 528/310; 528/315; 146/37
[58] Field of Search .................. 528/310, 315; 546/37

[56] References Cited

U.S. PATENT DOCUMENTS 4,845,223  7/1989  Seybold et al. .................. 546/37

FOREIGN PATENT DOCUMENTS 227 980   7/1870   European Pat. Off. .
445 577   9/1991   European Pat. Off. .
34 13 418 10/1985  Germany .

OTHER PUBLICATIONS

Japanese Abst. 58 894/1992.
Japanese Abst. 110 219/1988.

Primary Examiner—James J. Seidleck
Assistant Examiner—Duc Truong
Attorney, Agent, or Firm—Keil & Weinkauf

[57] ABSTRACT

Polymeric tetraaroxyperylene-3,4,9,10-tetracarboxylic diimides of the formula I

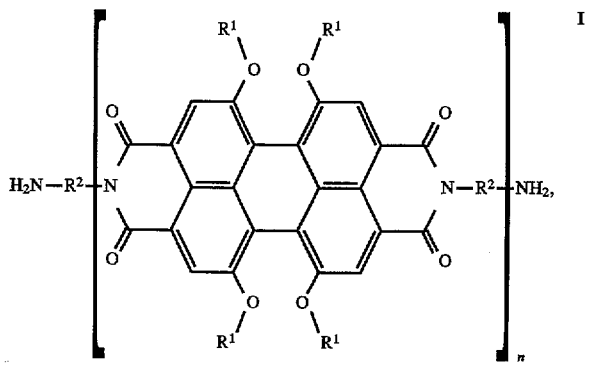

($R^1$: denotes identical or different aryl radicals which may be substituted by cyano, nitro, halogen, $C_1$–$C_{18}$-alkoxy, $C_5$–$C_7$-cycloalkyl and/or $C_1$–$C_{18}$-alkyl and may each contain up to 24 carbon atoms;

$R^2$: denotes $C_2$–$C_{30}$-alkylene groups whose carbon chain may be interrupted by from 1 to 10 oxygen atoms in ether function or by a phenylene or cyclohexylene group, or optionally $C_1$–$C_{10}$-alkylene- or oxygen-bridged $C_6$–$C_{30}$-arylene or cyclohexylene radicals;

n: is from 2 to 100), preparation thereof and use thereof and also tetraaroxyperylene-3,4,9,10-tetracarboxylic dianhydrides as intermediates therefor.

4 Claims, No Drawings

TETRAAROXYPERYLENE-3,4,9,10-TETRACARBOXYLIC POLYIMIDES

This application is a 371 of PCT/EP 94/01345 filed Apr. 28, 1994.

BACKGROUND OF THE INVENTION

Field of the Invention

The present invention relates to novel tetraaroxypery-lene-3,4,9,10-tetracarboxylic polyimides of the formula I

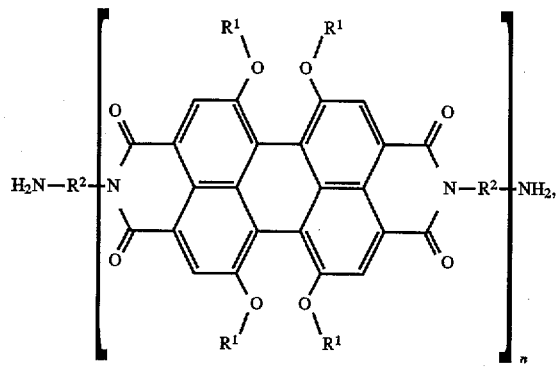

where

- $R^1$: denotes identical or different aryl radicals which may be substituted by cyano, nitro, halogen, $C_1$–$C_{18}$-alkoxy, $C_5$–$C_7$-cycloalkyl and/or $C_1$–$C_{18}$-alkyl and may each contain up to 24 carbon atoms;
- $R^2$: denotes $C_2$–$C_{30}$-alkylene groups whose carbon chain may be interrupted by from 1 to 10 oxygen atoms in ether function or by a phenylene or cyclohexylene group, or optionally $C_1$–$C_{10}$-alkylene- or oxygen-bridged $C_6$–$C_{30}$-arylene or cyclohexylene radicals;
- n: is from 2 to 100, and to the preparation of these polyimides and to their use in dye lasers, light collectors, printing inks and paints and for coloring plastics.

The invention also relates to the use of novel tetraaroxypery-lene-3,4,9,10-tetracarboxylic dianhydrides of the formula III

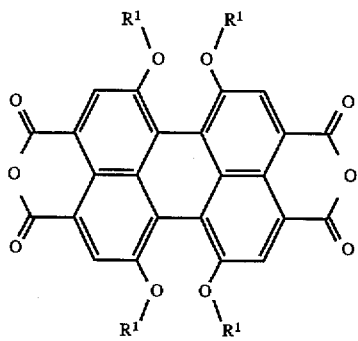

and to the corresponding tetraaroxyperylene-3,4,9,10-tetracarboxylic acids (IIa) as intermediates for preparing the polyimides I.

As will be known, there are many possible uses for fluorescent dyes; they are used for example for the flat-plate concentration of light in light collectors, for manufacturing dye lasers and daylight-fluorescent colors and also generally for coloring printing inks, paints and polymers.

For this the dyes have to have a number of properties which are high in particular for light collectors. They have to have high fluorescence, a broad absorption range, good separation of absorption and emission bands in the application medium, high lightfastness and good solubility and at the same time low tendency to migrate in the application medium.

DESCRIPTION OF THE RELATED ART

These requirements are difficult to meet at one and the same time. This is also true of the fluorescent dyes described in EP-A-227 980 and JP-A-53 894/1992, which are based on monomeric, tetrasubstituted perylene-3,4,9,10-tetracarboxylic diimides and which are in some instances not satisfactory as regards their migration resistance.

JP-A-110 219/1988 and EP-A-445 577 disclose unsubstituted perylene-3,4,9,10-tetracarboxylic polyimides which, however, are not used as fluorescent dyes.

It is an object of the present invention to provide fluorescent dyes which come particularly close to the required property profile.

SUMMARY OF THE INVENTION

We have found that this object is achieved by the above-defined tetraaroxyperylene-3,4,9,10-tetracarboxylic polyimides I.

The invention further provides a process for preparing the polyimides I, which comprises a) treating a tetraaroxyperylene-3,4,9,10-tetracarboxylic diimide of the formula II

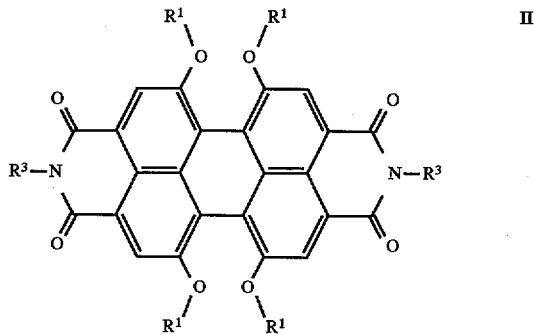

where the radicals $R^3$ are $C_1$–$C_{30}$-alkyl radicals whose carbon chain may be interrupted by from 1 to 10 oxygen atoms in ether function, $C_5$–$C_7$-cycloalkyl or phenyl radicals which may each be substituted by up to 2 $C_1$–$C_4$-alkyl groups, with a base in a polar, protic solvent, and b) polycondensing the tetraaroxyperylene-3,4,9,10-tetracarboxylic dianhydride obtained in step a), of the general formula III

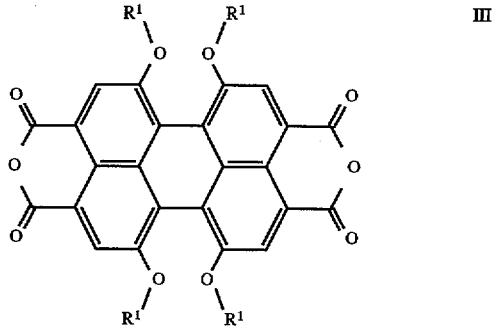

with a diamine of the general formula IV $$H_2N—R^2—NH_2 \qquad IV$$

in the presence of a polar solvent initially under acid and then under basic catalysis at from 170° to 200° C.

The invention also provides for the use of the polyimides I for manufacturing dye lasers and light collectors and for pigmenting printing inks, paints and plastics.

Lastly the present invention provides the tetraaroxyperylene-3,4,9,10-tetracarboxylic dianhydrides III and their corresponding tetraaroxyperylene- 3,4,9,10-tetracarboxylic acids (IIIa) as intermediates for preparing the polyimides I.

DESCRIPTION OF THE PREFERRED EMBODIMENTS $R^1$ is aryl, such as naphthyl, anthryl or in particular phenyl. The aryl radicals can be substituted by cyano, nitro, halogen, in particular chlorine, $C_1$–$C_{18}$-alkoxy, $C_5$–$C_7$-cycloalkyl, especially cyclohexyl, and/or $C_1$–$C_{18}$-alkyl, and in each case can contain up to 24 carbon atoms. The $R^1$ radicals can be identical or different, but are preferably identical.

Examples of the $C_1$–$C_{18}$-alkoxy and alkyl groups suitable for use as substituents are:

methoxy, ethoxy, propoxy, isopropoxy, butoxy, isobutoxy, sec-butoxy, tert-butoxy, pentyloxy, isopentyloxy, neopentyloxy, hexyloxy, heptyloxy, octyloxy, 2-ethylhexyloxy, nonyloxy, decyloxy, undecyloxy, dodecyloxy, tridecyloxy, tetradecyloxy, pentadecyloxy, hexadecyloxy, heptadecyloxy and octadecyloxy and also further branched radicals of this kind;

methyl, ethyl, propyl, isopropyl, butyl, isobutyl, sec-butyl, tert-butyl, pentyl, isopentyl, neopentyl, tert-pentyl, hexyl, 2-methylpentyl, heptyl, octyl, 2-ethylhexyl, nonyl, decyl, undecyl, dodecyl, tridecyl, tetradecyl, pentadecyl, hexadecyl, heptadecyl and octadecyl and also further branched radicals of this kind.

Examples of preferred substituted aryl radicals are 4-tert-butylphenyl, 2-cyclohexyl-4-methylphenyl, 2- and 4-cyclohexyl-phenyl, 4-hexyloxyphenyl, 2-phenylphenyl, 4-cyanophenyl-o-nitro-phenyl, benzylphenyl and 2-benzyl-4-chlorophenyl.

The $R^2$ groups are preferably aliphatic, cycloaliphatac or aromatic groups.

Suitable alkylene groups generally contain from 2 to 30, preferably from 2 to 10, carbon atoms. Examples are ethylene, 1,2- and 1,3-propylene, 1,2-, 1,3-, 1,4- and 2,3-butylene, 1,2-, 1,3-, 1,4-, 1,5-, 2,3- and 2,4-pentylene, hexamethylene, heptamethylene, octamethylene, nonamethylene and decamethylene and also further branched radicals of this kind.

In addition, the carbon chain in these groups can be interrupted by from 1 to 10 oxygen atoms in ether function or by phenylene or cyclohexylene. Examples are (Ph= phenylene, $C_6H_4$=cyclohexylene):

—(CH$_2$)$_2$—O—(CH$_2$)$_2$—, —[(CH$_2$)$_2$—O]$_2$—(CH$_2$)$_2$—, —[(CH$_2$)$_2$—O]$_3$—(CH$_2$)$_2$—, —(CH$_2$)$_3$—O—(CH$_2$)$_4$—O—(CH$_2$)$_3$—, —(CH$_2$)$_3$—O—[(CH$_2$)$_2$—O]$_2$—(CH$_2$)$_3$—, —CH$_2$—Ph—CH$_2$— and —CH$_2$—C$_6$H$_4$—CH$_2$—.

Suitable cyclic groups $R^2$ in particular are cyclohexylene and phenylene, but also naphthylene. More particularly, two arylene or cyclohexylene radicals can also be bridged via oxygen or $C_1$–$C_{10}$-alkylene. Examples of these groups are (m=from 1 to 10):

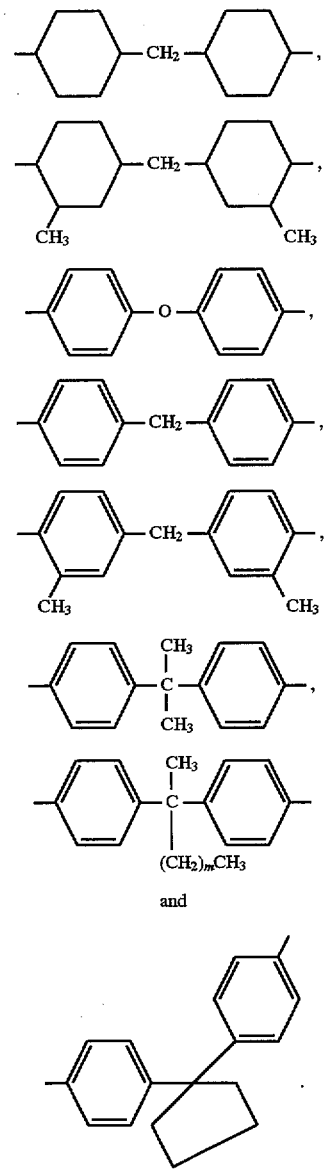

and

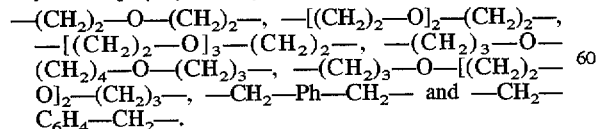

The variable n finally denotes an average value for the perylenediimide units present in the polyimide I, and generally ranges from 2 to 100, especially from 10 to 50, particularly preferably from 20 to 40.

The polyimides I according to the present invention are notable altogether for excellent properties: they exhibit high lightfastness, high thermal stability, high fluorescence and a broad absorption range. They are very readily soluble despite their molecular size, while exhibiting only minimal migration tendencies in the application media. Moreover, they film easily, and form homogeneous films on glass or plastic.

The novel process for preparing the polyimides I proceeds in two stages via the novel tetraaroxyperylene-3,4,9,10-tetracarboxylic dianhydrides III or the corresponding acids (IIIa) as intermediates.

The starting materials used in the synthesis of the anhydrides III in step a) are the above-defined tetraaroxyperylene-3,4,9,10-tetracarboxylic diimides II.

Suitable $R^3$ on the imide nitrogen atom is $C_1$–$C_{30}$-alkyl, preferably $C_1$–$C_{18}$-alkyl as mentioned for $R^1$, $C_5$–$C_7$-cycloalkyl, especially cyclohexyl, or phenyl.

The carbon chain of the alkyl radicals can be interrupted by from 1 to 10 oxygen atoms in ether function. Examples are 2-methoxy-, 2-ethoxy-, 2-propoxy-, 2-isopropoxy- and 2-butoxyethyl, 2- and 3-methoxypropyl, 2- and 3-ethoxypropyl, 2- and 4-ethoxybutyl, 2- and 4-isopropoxybutyl, 5-ethoxypentyl, 6-methoxyhexyl, 4-oxa-6-ethyldecyl, 3,6-dioxaheptyl, 3,6-dioxaoctyl, 3,6-dioxadecyl, 3,6,9-trioxadecyl and 3,6,8-trioxaundecyl.

The cycloalkyl and phenyl radicals can be substituted by up to 2 $C_1$–$C_4$-alkyl groups as likewise mentioned above.

The perylimides II are known from EP-A-227 980 and can be prepared as described therein, by reaction of the tetrachloroperylimides with the corresponding arylates.

In step a) of the process of the invention, a perylimide II is converted into the corresponding anhydride III by the action of a base in the presence of a polar protic solvent. The acid (III) itself is not stable, and changes into the anhydride virtually immediately.

Suitable bases are in particular inorganic bases such as sodium hydroxide and potassium hydroxide.

As customary for such reactions, the base is used in excess, i.e. generally in amounts of from 1 to 10 mol per 10 mmol.

Suitable polar, protic solvents are in particular $C_1$–$C_{10}$-alkanols such as propanol, isopropanol, n-butanol, n-hexanol, n-decanol, preferably tert-butanol. Advantageously a small amount of water, generally from 0.1 to 0.4 mol per mmole of II, is added to facilitate the removal of the product.

Similarly, the amount of solvent is not critical. Customary amounts are from 0.5 to 1.2 mol per mmole of II.

Advantageously, step a) of the process of the invention is performed by heating the mixture of perylene diimide II, base and solvent under reflux, i.e. at about 80°–140° C., for several h, generally from 10 to 48 h. After cooling down to room temperature, the organic phase can then be separated off. The anhydride III can be isolated in a conventional manner by precipitation with an acid, filtration, washing and drying.

In step b) of the process of the invention, the anhydride III obtained in a) and a diamine IV are polymerized.

This polycondensation is preferably carried out in the presence of a polar solvent initially under acid and then under base catalysis.

Suitable polar solvents are the solvents used in the preparation of polyimides. Preferred examples are cresol, dimethylformamide, dimethylacetamide, N-methylpyridone, 1,3-dimethyl-3,4,5,6-tetrahydropyrimidin-2-one. The solvent is customarily used in amounts of from 0.8 to 2 mol, preferably about 1 mol, per 10 mmol of diamine IV.

The preferred acid catalyst is, for example, benzoic acid. Generally, from 2 to 4 mol, in particular 2 mol, of catalyst are used per mole of III. Particularly suitable basic catalysts are for example quinoline and isoquinoline, which are customarily likewise used in amounts from about 2 to 4 mol, preferably 2 mol, per mole of III.

The reaction temperature is generally from 170° to 200° C.

Advantageously, the polycondensation is advantageously carried out by heating a mixture of diamine IV, solvent, anhydride III and acid catalyst at the reaction temperature for initially from about 8 to 12 h and, after addition of the basic catalyst, customarily for a further 15–24 h. After cooling down to room temperature, the polyimide I can be separated from the reaction mixture by dissolving in chloroform and reprecipitated by addition of methanol.

The process of the invention is notable for the good yields and high purity of the polyimides I obtained.

The polyimides I are advantageously useful for the purposes customary for fluorescent dyes, such as the manufacture of light collectors and dye lasers, which is described in EP-A-227 980 and DE-A-34 13 418 respectively, and the references cited in each case. They can also be used for pigmenting printing inks, paints, including daylight-luminescent colors, and plastics.

EXAMPLES

Preparation of polymeric tetraaroxyperylene-3,4,9,10-tetracarboxylic diimides I' a) Preparation of the tetraaroxyperylene-3,4,9,10-tetracarboxylic dianhydrides III'

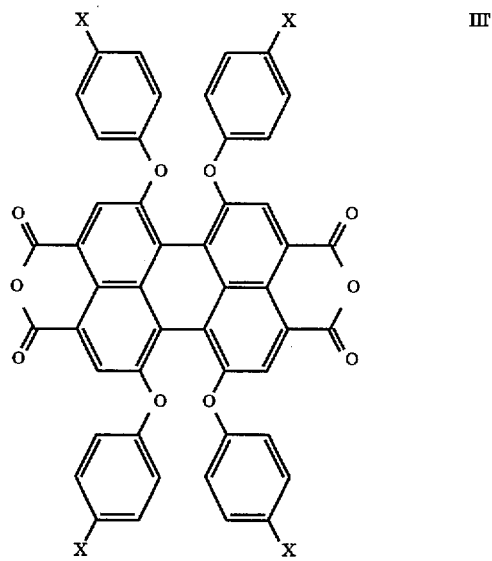

A mixture of 0.74 mmol of a perylimide II

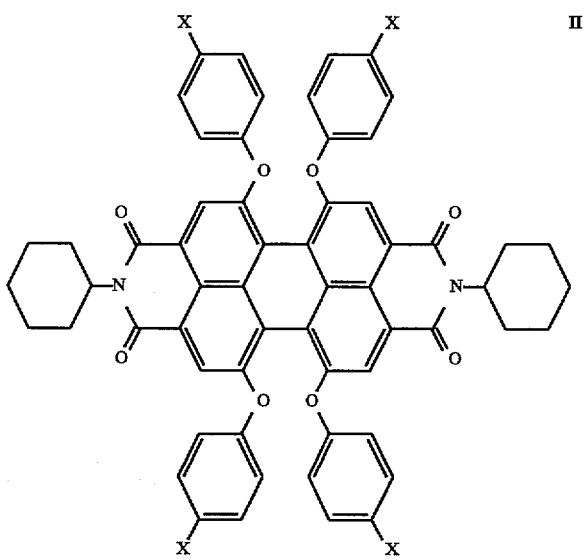

and 6.0 g of potassium hydroxide, 60 ml of tert-butanol and 3 ml of water was refluxed with stirring for 25 h. After cooling down to room temperature, the liquid organic phase was separated off and admixed with the same volume of 2N hydrochloric acid.

After 8 h the precipitate was filtered off, washed neutral with water and dried at 100° C. under reduced pressure. To further purify the product, it was again dissolved in 5% strength by weight ethanolic sodium hydroxide solution and reprecipitated by addition of 2N hydrochloric acid.

Further details concerning these experiments and their results are listed in Table 1.

TABLE 1

Tetraaroxyperylene-3,4,9,10-tetracarboxylic dianhydrides III'

| Ex. | X | Yield [%] | m.p. [°C.] | IR (KBr) $\gamma$(C=O) [cm$^{-1}$] | Absorpt. UV-VIS (CHCl$_3$) $v_{max}$ [nm] | Fluorescence (CHCl$_3$) $\lambda_{max}$ [nm] | $^1$H-NMR (CDCl$_3$) $\delta$ (4H, arom. H; 8H, acrom. H) | MS (70 eV) obs.; calc. | Elemental analysis % C: obs.; calc. | % H: obs.; calc. |
|---|---|---|---|---|---|---|---|---|---|---|
| 1 | —C(CH$_3$)$_3$ | 82 | >300 | 1780, 1740 | 585 | 615 | 8.20; 7.23, 6.98 | 985.14; 985.14 | 78.06; 78.02 | 5.52; 5.73 |
| 2 | —H | 88 | >300 | 1700, 1660 | 571 | 610 | 8.10 7.18, 6.82 | 760,12; 760.13 | 75.73; 75.79 | 3.22; 3.16 | b) Preparation of the polymeric tetraaroxyperylene-3,4,9,10-tetracarboxylic diimides I'

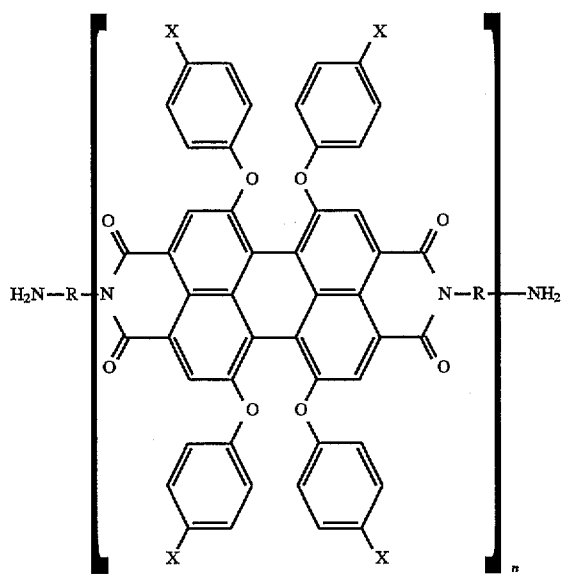

A mixture of 0.3 mmol of a diamine IV'

$$H_2N\text{—}R\text{—}NH_2 \qquad IV'$$

dissolved in 3 ml of m-cresol, 0.3 mmol of anhydride III' and 0.6 mmol of benzoic acid was heated to 190° C. with stirring under a stream of argon for 9 h. After addition of 0.6 mmol of isoquinoline, dissolved in 0.3 ml of m-cresol, the polycondensation was continued at 190° C. for a further 19 h.

The viscous reaction mixture was then cooled down to room temperature, and chloroform was added. The polymer solution obtained was filtered, the filtrate was concentrated, and the polyimide I' was precipitated with methanol, recrystallized and filtered off on a G4 glass filter at atmospheric pressure.

All the polyimides I' obtained exhibited the characteristic vibrations for aromatic imides in six-membered rings at 1700 cm$^{-1}$ and for carbonyl groups bonded to two aromatic rings, at 1660 cm$^{-1}$, and were thermally stable at up to 350° C. in air and under nitrogen.

Further details relating to these experiments and their results are collated in Tables 2 and 3.

TABLE 2

Polymeric tetraaroxyperylene-3,4,9,10-tetracarboxylic diimides I'

| Ex. | X | R | n | Yield [%] | Absorption UV-VIS (CHCl$_3$) $\lambda_{max}$ [nm] | Fluorescence (CHCl$_3$) $\lambda_{max}$ [nm] |
|---|---|---|---|---|---|---|
| 3 | —C(CH$_3$) | —(CH$_2$)$_9$— | 20–25 | 94 | 589 | 615 |
| 4 | —C(CH$_3$) | —Ph—O—Ph—* | 20–25 | 95 | 608 | 622 |
| 5 | —C(CH$_3$) | —Ph—CH$_2$—Ph— | 20–25 | 90 | 592 | 619 |
| 6 | —H | —Ph—O—Ph— | 20–25 | 95 | 599 | 621 |

| | Elemental analysis | | | | | | | | | $\eta$ |
|---|---|---|---|---|---|---|---|---|---|---|
| | % C: | | % H: | | % N: | | $M_n$$^a$ | $M_w$$^b$ | | (CHCl$_3$, 25° C.)$^c$ |
| Ex. | obs.; | calc. | obs.; | calc. | obs.; | calc. | (GPC) | (GPC) | $M_w/M_n$ | [dl/g] |
| 3 | 78.80; | 79.80 | 6.68; | 6.74 | 2.32; | 2.53 | 11290 | 22590 | 2.0 | 0.24 |
| 4 | 78.94; | 79.42 | 5.45; | 5.51 | 2.12; | 2.44 | 23010 | 46860 | 2.0 | 0.40 |
| 5 | 79.40; | 80.60 | 5.74; | 5.80 | 2.47; | 2.44 | 30450 | 64070 | 2.1 | 0.52 |
| 6 | 76.85; | 77.90 | 3.35; | 3.49 | 3.13; | 3.03 | 6950 | 34840 | 5.0 | 0.14 |

*Ph = phenylene

TABLE 2-continued

Polymeric tetraaroxyperylene-3,4,9,10-tetracarboxylic diimides I'

[a] $M_n$: number average molecular weight
[b] $M_w$: weight average molecular weight
[c] η: inherent viscosity

TABLE 3

Investigation of the solubility of polyimides I' (0.5 g/100 ml of solvent)

| Ex. | m-Cresol | n-Methyl-pyrrolidone | Dimethyl-acetamide | Chloroform | Methylene chloride | Tetrahydro-furan | Toluene |
|---|---|---|---|---|---|---|---|
| 3 | +++ | +++ | ++ | +++ | +++ | +++ | ++ |
| 4 | +++ | ++ | +− | +++ | +++ | +− | +− |
| 5 | +++ | ++ | +− | +++ | +++ | +− | +− |
| 6 | ++ | ++ | − | +− | +− | +− | − |

+++ soluble at room temperature
++ soluble on heating
+− partly soluble
− insoluble

We claim:

1. Tetraaroxyperylene-3,4,9,10-tetracarboxylic polyimides of the formula I

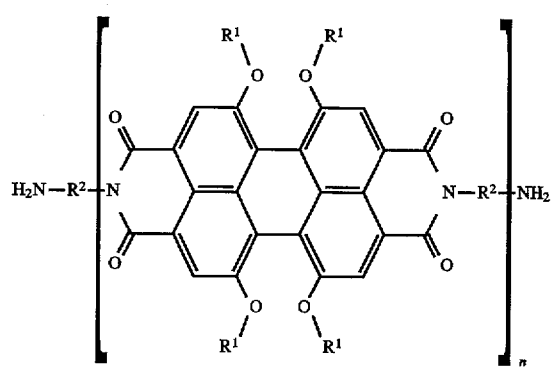

where $R^1$ denotes identical or different aryl radicals which may be substituted by cyano, nitro, halogen, $C_1$–$C_{18}$-alkoxy, $C_5$–$C_7$-cycloalkyl and/or $C_1$–$C_{18}$-alkyl and may each contain up to 24 carbon atoms;

$R^2$ denotes $C_2$–$C_{30}$-alkylene groups whose carbon chain may be interrupted by from 1 to 10 oxygen atoms in ether function or by a phenylene or cyclohexylene group, or optionally $C_1$–$C_{10}$-alkylene- or oxygen-bridged $C_6$–$C_{30}$-arylene or cyclohexylene radicals;

n is from 2 to 100.

2. A process for preparing tetraaroxyperylene-3,4,9,10-tetracarboxylic polyimides of the formula I as set forth in claim 1, which comprises a) treating a tetraaroxyperylene-3,4,9,10-tetracarboxylic diimide of the formula II

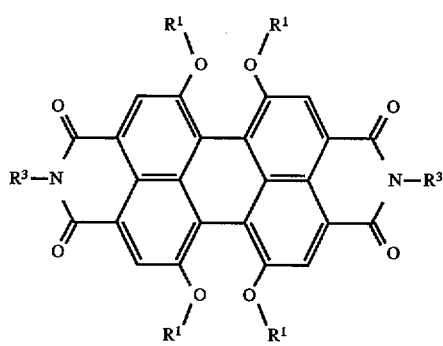

where $R^1$ and $R^2$ are as described in claim 1 and where the radicals $R^3$ are $C_1$–$C_{30}$-alkyl radicals whose carbon chain may be interrupted by from 1 to 10 oxygen atoms in ether function, $C_5$–$C_7$-cycloalkyl or phenyl radicals which may be substituted by up to 2 $C_1$–$C_4$-alkyl groups, with a base in a polar, protic solvent, and b) polycondensing the tetraaroxyperylene-3,4,9,10-tetracarboxylic dianhydride obtained in step a), of the formula III

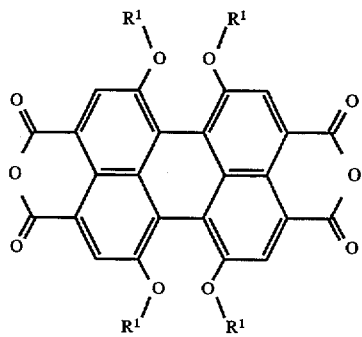

with a diamine of the formula IV

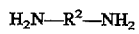

in the presence of a polar solvent initially under acid and then under basic catalysis at from 170° to 200° C.

3. Tetraaroxyperylene-3,4,9,10-tetracarboxylic dianhydrides of the formula III

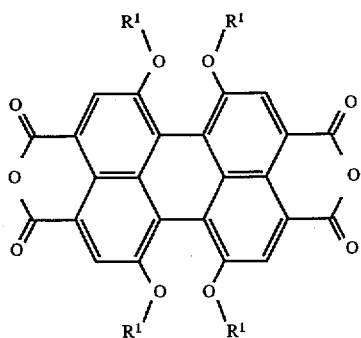

III where the radicals $R^1$ denote identical or different aryl radicals which may be substituted by cyano, nitro, halogen, $C_1$–$C_{18}$-alkoxy, $C_5$–$C_7$-cycloalkyl and/or $C_1$–$C_{18}$-alkyl and which may each contain up to 24 carbon atoms, and the corresponding tetraaroxyperylene-3,4,9,10-tetracarboxylic acids (IIIa).

4. A process for manufacturing dye lasers and light collectors and for pigmenting printing inks, paints and plastics, which comprises using tetraaroxyperylene-3,4,9,10-tetracarboxylic polyimide, of the formula I as set forth in claim 1.

* * * * *